US008491917B1

(12) United States Patent
Bender

(10) Patent No.: US 8,491,917 B1
(45) Date of Patent: Jul. 23, 2013

(54) TREATMENT OF MIGRAINE HEADACHE WITH DIFFUSION OF TOXIN IN NON-MUSCLE RELATED AREAS OF THE HEAD

(76) Inventor: William J. Bender, Beverly Hills, CA (US)

( * ) Notice: Subject to any disclaimer, the term of this patent is extended or adjusted under 35 U.S.C. 154(b) by 0 days.

(21) Appl. No.: 13/478,876

(22) Filed: May 23, 2012

Related U.S. Application Data

(60) Provisional application No. 61/609,817, filed on Mar. 12, 2012.

(51) Int. Cl.
*A61K 39/08* (2006.01)
*A61P 23/02* (2006.01)
*C07K 14/00* (2006.01)

(52) U.S. Cl.
USPC ..... 424/239.1; 514/21.2; 530/350; 435/252.7

(58) Field of Classification Search
USPC ..... 424/239.1; 435/252.7; 514/21.2; 530/350
See application file for complete search history.

(56) References Cited

U.S. PATENT DOCUMENTS

| 5,714,468 | A | 2/1998 | Binder |
| 5,721,215 | A | 2/1998 | Aoki et al. |
| 6,458,365 | B1 | 10/2002 | Aoki et al. |
| 7,655,244 | B2 | 2/2010 | Blumenfeld |
| 7,704,511 | B2 | 4/2010 | Turkel et al. |
| 7,981,433 | B2 | 7/2011 | Blumenfeld |

OTHER PUBLICATIONS

Andrew Blllmenfeld, et al. "Method of Injection of OnabotulinumtoxinA for Chronic Migraine: A Safe, Well-Tolerated, and Effective Treatment Paradigm Based on the PREEMPT Clinical Program", Headache, 2010 American Headache Society, ISSN 0017-8748; doi: 10.111/j.1526-4610.2010.01766.x, Wiley Periodicals, Inc.
Lidija Bach-Rojecky, et al., "Central Origin of the Antinociceptive Action of Botulinum Toxin Type A", Pharmacology, Biochemistry and Behavior 94 (2009) 234-238, Elsevier, Inc.
Ritu Bahl, "Local Anesthesia in Dentistry", Anesth Prog 5 1:138-142 (2004), American Dental Society of Anesthesiology.
Stanley F. Malamed, et al. "Intraoral Maxillary Nerve Block: An Anatomical and Clinical Study", Anesthesia Progress, Mar./Apr. 1983, pp. 44-48.

*Primary Examiner* — Taeyoon Kim

(57) ABSTRACT

A method for treating a patient with migraine headache in accordance with the present invention generally includes administering to the patient a therapeutically effective amount of a Botulinum toxin in a pharmaceutically safe form with the administration being on the trigeminal cervical system, for enabling axonal transport of the neurotoxin from distal to central sites. More specifically, the administration includes extramuscular injection of the neurotoxin over the aponeurotic fascia of the scalp for enabling the neurotoxin to diffuse into distal sensory nerves, in order to enable concentration over the occipital-parietal-frontal head region.

5 Claims, 1 Drawing Sheet

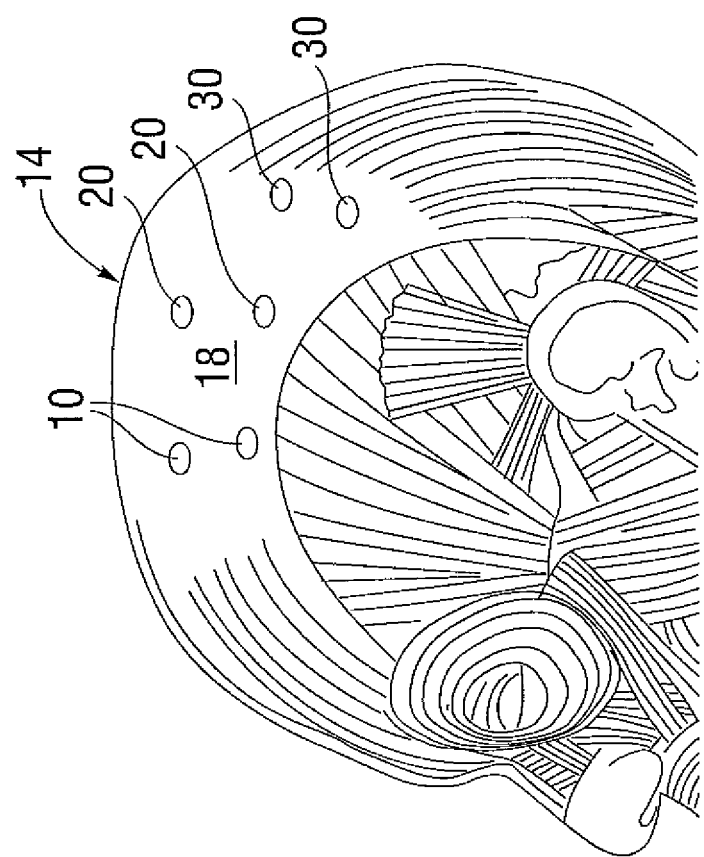

TREATMENT OF MIGRAINE HEADACHE WITH DIFFUSION OF TOXIN IN NON-MUSCLE RELATED AREAS OF THE HEAD

This patent application claims the benefit of U.S. Provisional Application 61/609,817, filed Mar. 12, 2012.

Botulinum toxins have been used to treat migraine headache. This is well established in the art. By way of example only, see U.S. Pat. Nos. 5,714,468, 5,721,215, 6,458,365, 7,655,244, 7,704,511, and 7,981,433. All of these references are to be incorporated herewith in their entirety. These patents include: Binder; Botulinum toxin injections to the head for migraine, Blumenfeld; Botulinum toxin injections to the sphenopalatine ganglion, nasal approach and vascular approach, suture line technique (these are not foramina or exit points); Aoki; Tension type headache treatment with Botulinum toxin, and Turkel; 31 sites as for the FDA approved protocol for chronic migraine.

Heretofore, onabotulinumtoxinA has been FDA approved for treatment of migraine headache. The dose used is 155 to 195 units, with a dilution of 2 cc per 100 units of onabotulinumtoxinA. Doses ranging from 25 units to 260 units have been used to treat various headache disorders. These have involved intra-muscular injections in fixed sites and follow the pain sites.

Botulinum toxin side effects are usually due to local diffusion to surrounding muscles producing unwanted weakness.

SUMMARY OF THE INVENTION

The present invention is directed to treatment of migraine headaches with Botulinum toxin (and/or endopeptidase) by adjusting the toxin concentration and volume to establish optimum diffusion of toxin in non-muscle related areas of the head, such as fascia injections to the scalp. The improvement avoids side effects such as muscle paralysis and reduces doses overall, through the use of low concentration/high volume injections in fascia on the scalp.

In general, the present invention aims to minimize the side effects present with prior injection techniques and uses a novel injection approach to achieve this goal. In addition, this invention aims to increase the efficacy across multiple headache types including chronic and episodic migraine, post-traumatic headache, post-craniotomy headache, tension type headache and medication overuse headache. This invention focuses the medication on the sites of maximal benefit; i.e., the trigemino-cervical nerves.

The technique involves administration to allow for maximizing the dose and thus the effect on the trigeminal cervical system while minimizing any side effects.

The method may include Botulinum toxins such as Botulinum toxin A, B, C, D, E, F, and G.

Alternatively, the neurotoxin may include an Endotoxin such as, for example, wherein the Endotoxin is an endopeptidase derived from Botulinum toxin.

BRIEF DESCRIPTION OF THE DRAWINGS

The advantages and features of the present invention will be better understood by the following description when considered in conjunction with the accompanying drawing, in which:

FIG. 1 is a diagram of injection sites in accordance with the present invention showing the Frontal (10), Parietal (20) and Occipital (30) aponeurotic fascia in head 14.

DETAILED DESCRIPTION

In general, dilute Botulinum toxin: about 4-10 cc per 100 units is injected over the aponeurotic fascia, not into muscle, allowing the toxin to diffuse into distal sensory nerve endings that are concentrated over the occipital parietal-frontal head regions. (There is no muscle in this location) No muscle weakness results as all the injections are in non-muscular regions. The toxin diffuses in a broad area due to the dilution; allowing for a decrease in the number of injection sites. Botulinium toxin is delivered to the distal sensory nerve endings 10 in the scalp 14. See FIG. 1. These include unmyelinated C fibers.

Importantly, the present invention utilizes the proximal axonal transport of Botulinum toxins from distal to central sites.

CLINICAL EXAMPLES

Case 1

43 year old woman, with a long standing history of migraine, suffers with headache on twenty (20) days out of each month and requires triptan medication on twelve (12) days out of each month to try and control her more disabling headaches. She meets criteria for chronic migraine complicated by medication overuse headache. She fails to respond to numerous preventive medications such as Topiramate and Propranolol. She is treated with onabotulinumtoxinA using the PREEMPT injection protocol with fixed sites and follow-the-pain injections. Total dose given 195 units. She has developed neck pain, brow ptosis and no improvement in her headache frequency after three (3) treatment cycles.

She is then treated with the focused injection protocol as outlined in this invention.

OnabotulinumtoxinA is diluted as follows: 100 units in 8 cc of normal saline (0.1 ml contains 1.25 units).

Injection sites and dosing as follows:

8 cc dilution

Frontal aponeurotic fascia 5 units each side (0.4 cc per side)
Parietal aponeurotic fascia 5 units each side (0.4 cc per side)
Occipital aponeurotic 5 units each side (0.4 cc per side)
Total dose: 30 units The patient reports fewer migraine headaches of lesser duration and intensity. The patient does not develop neck weakness or pain as the neck musculature is not injected. The patient does not develop brow ptosis as the frontalis muscle is not injected.

Lower dosing of onabotulinumtoxinA is used as the medication is delivered in a focus where it will have the most benefit; i.e.: no unnecessary flooding or extravasation of medication to unwanted sites.

Case 2

38 year old man with a history of chronic migraine headaches is successfully treated with onabotulinumtoxinA using the PREEMPT injection sites. Unfortunately, he develops temporalis wasting which gives him an hour-glass appearance due to the toxin adversely affecting the temporalis muscle region. He is seen for consultation to review other treatment options. Because onabotulinumtoxinA treatments have been successful he wishes to continue with these but wants to avoid the side effects he experienced. He is successfully treated using the method of onabotulinumtoxinA outlined in the above invention.

100 units of onabotulinumtoxinA is diluted in 4 cc of normal saline. The more concentrated solution is chosen in this case to limit any possible diffusion to the temporalis muscle region. Each 0.1 ml contains 2.5 units of onabotulinumtoxin A.

Frontal aponeurotic fascia 5 units (2.5 units in 2 locations about 1 inch apart) on each side (0.2 cc).
Parietal aponeurotic fascia 5 units (2.5 units in 2 locations about 1 inch apart) on each side (0.2 cc).
Occipital aponeurotic fascia 5 units (2.5 units in 2 locations about 1 inch apart) on each side (0.2 cc).
Total of 30 units.

The treatment is well tolerated and the patient does not develop any temporalis wasting.

Case 3:
64 year old bald man has a long history of migraines dating back to his teens. He now presents with headaches mainly involving the vertex of the head. These occur about 8 days a month. They are disabling, worsened by head movement and associated with sensitivity to light and noise. These are diagnosed as episodic migraine. His neurological examination and brain imaging studies are normal for age. The only exception is that he has senile ptosis. Treatment options are reviewed with the patient. He wants to try a preventive approach to avoid getting these disabling headaches. He wants to try onabotulinumtoxinA. However, injections of the frontalis are contra-indicated as these will worsen the senile brow ptosis and in addition the headaches are only located over the vertex of the head.

OnabotulinumtoxinA is successfully used to treat his headaches using the method described in this invention.

100 units of onabotulinumtoxinA is diluted in 10 cc of normal saline. The toxin is dawn up into 1 cc syringes with a 30 gauge half inch needle used for administration to the vertex area of the head. The vertex is divided into a grid-like area with injections placed in the center of each square.

Each injection is 0.2 cc which contains 2 units of onabotulinumtoxinA: 10 cc dilution per 100 units (0.1 unit per 1 cc). The width of the square is one inch as this encompasses the diffusion area of this dilute toxin. The grid consists of 9 squares similar to a tic tac toe diagram with each square measuring one inch so that the total treated area is 3 inches by 3 inches. The injections are done in the center of each square and at the 4 outside corners for a total of 13 sites. The needle is inserted deep into the aponeurotic fascia. Total dose administered 26 units. The patient's headache frequency and intensity improve and there is no worsening of his senile brow ptosis.

Although there has been hereinabove described a specific treatment of migraine headache with diffusion of toxin in non-muscle related areas of the head in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A method for treating a human patient with migraine headache, said method comprising administering to the patient a therapeutically effective amount of diluted Botulinum toxin in a pharmaceutically safe form wherein said diluted Botulinum toxin is about 4-10 cc normal saline per 100 units of Botulinum toxin, said administration comprising extramuscular injection into one or more of the frontal, parietal and occipital aponeurotic fascia in the scalp.

2. The method according to claim 1 wherein the Botulinum toxin is Botulinum toxin A.

3. The method according to claim 1 wherein the Botulinum toxin is Botulinum toxin B.

4. The method according to claim 1 wherein the Botulinum toxin is an endopeptidase derived from Botulinum toxin.

5. The method according to claim 2 wherein the Botulinum toxin A is onabotulinumtoxinA.

* * * * *

UNITED STATES PATENT AND TRADEMARK OFFICE
CERTIFICATE OF CORRECTION

PATENT NO.         : 8,491,917 B1
APPLICATION NO.    : 13/478876
DATED              : July 23, 2013
INVENTOR(S)        : William J. Binder Page 1 of 1

It is certified that error appears in the above-identified patent and that said Letters Patent is hereby corrected as shown below:

On the Title Page

Item 12 delete "Bender" and insert --Binder-- in its place.

Item 76 delete "Bender" and insert --Binder-- in its place.

Signed and Sealed this
Twenty-eighth Day of January, 2014

Michelle K. Lee
*Deputy Director of the United States Patent and Trademark Office*